United States Patent [19]

Noren et al.

[11] Patent Number: 5,427,112
[45] Date of Patent: Jun. 27, 1995

[54] DEVICE FOR ANALYZING THE FUNCTION OF A HEART

[75] Inventors: Kjell Noren, Solna; Kurt Hoegnelid, Vaesterhaninge, both of Sweden

[73] Assignee: Siemens Elema AB, Solna, Sweden

[21] Appl. No.: 51,250

[22] Filed: Apr. 23, 1993

[30] Foreign Application Priority Data

Dec. 18, 1992 [SE] Sweden ................................ 9203882

[51] Int. Cl.$^6$ ............................................. A61B 5/00
[52] U.S. Cl. ................................... 128/702; 128/699; 364/413.06
[58] Field of Search .......................... 607/18, 24, 23; 128/699, 702, 705, 700, 696; 364/413.06

[56] References Cited

U.S. PATENT DOCUMENTS

| | | | |
|---|---|---|---|
| 3,602,706 | 8/1971 | Levitt | 128/696 |
| 4,417,306 | 11/1983 | Citron et al. | |
| 4,453,551 | 6/1984 | Anderson et al. | |
| 4,733,667 | 3/1988 | Olive et al. | 607/24 |
| 4,812,976 | 3/1989 | Lundy | 364/413.06 |
| 4,870,578 | 9/1989 | Vysin et al. | |
| 4,905,708 | 3/1990 | Davies | |
| 5,042,497 | 8/1991 | Shapland | |
| 5,088,491 | 2/1992 | Schaldach | 607/18 |

FOREIGN PATENT DOCUMENTS 0220916 5/1987 European Pat. Off.

OTHER PUBLICATIONS

"Phase Plane Plot of Electrograms as a Marker of Ventricular Electrical Instability During Acute Ischemia: Initial Experimental Results and Potential Clinical Applications," Karaguezian et al., PACE, vol. 15, Nov., 1992, pp. 2188∝2193.

*Primary Examiner*—William E. Kamm
*Assistant Examiner*—Kennedy J. Schaetzle
*Attorney, Agent, or Firm*—Hill, Steadman & Simpson

[57] ABSTRACT

A device for analyzing the function of a heart, containing a measurement unit for generating a first measurement signal related to a first electrical or mechanical heart variable and an evaluation unit for evaluating the measurement signal, further contains a circuitry for generating a parameter signal related to a heart variable, the evaluation unit analyzing the related values for the measurement signal and the parameter signal. The device can be used for detecting a number of functional aberrations, such as bradycardia, tachyarrhythmia, retrograde conduction, ischemia and ectopia, and for controlling pacemakers and defibrillators.

28 Claims, 11 Drawing Sheets

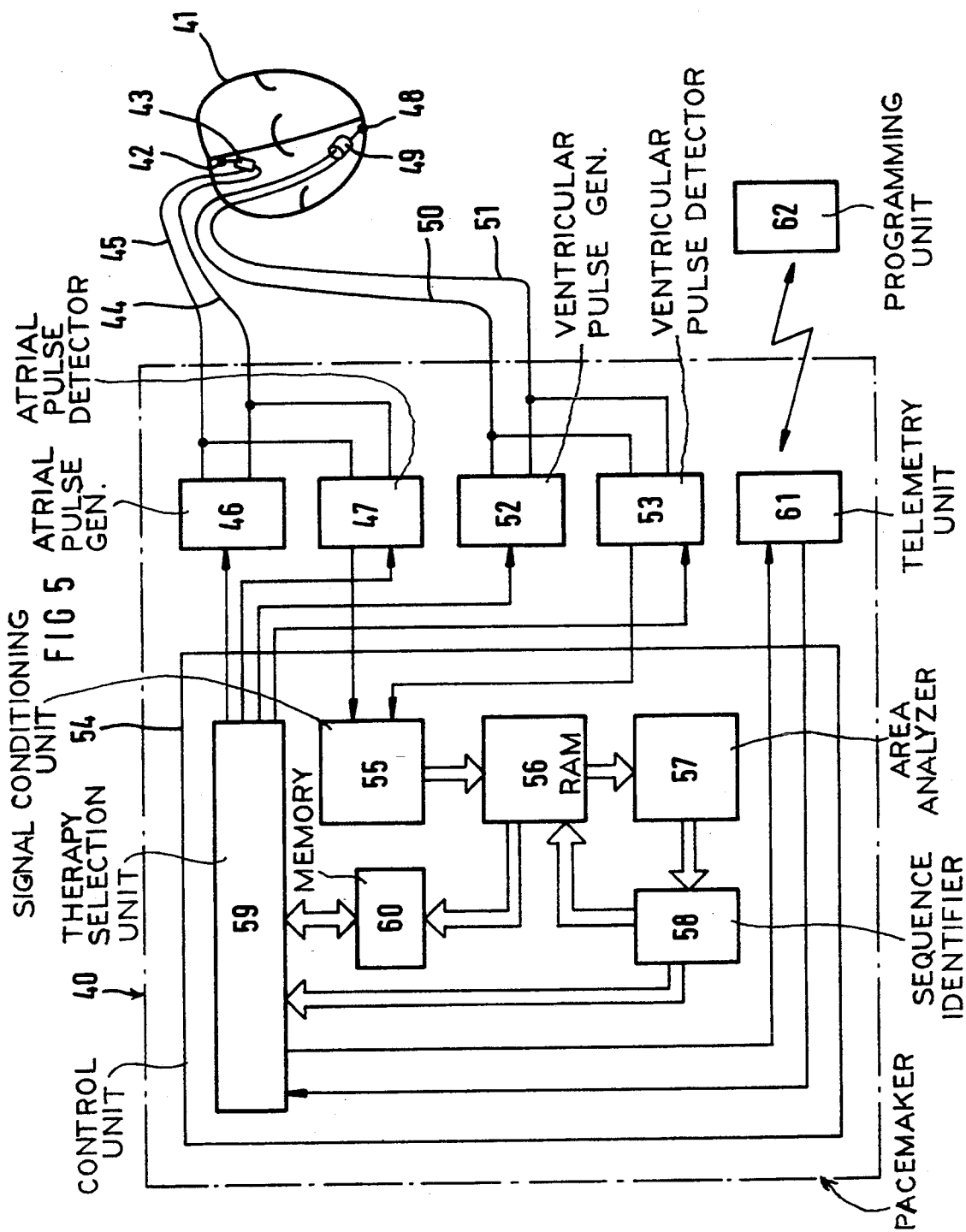

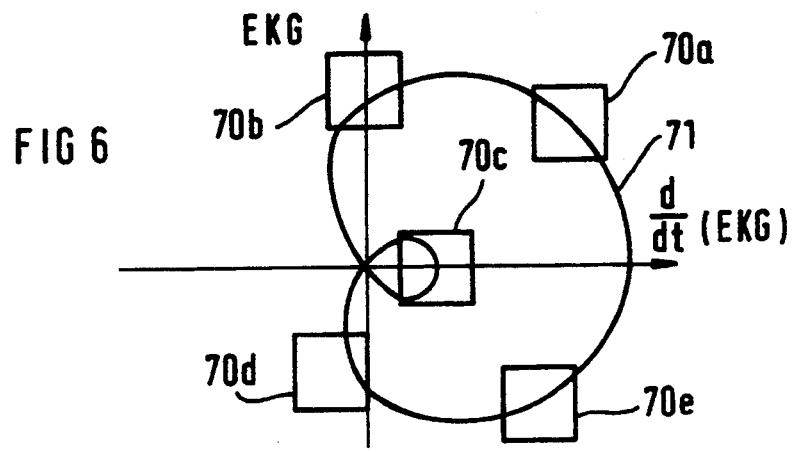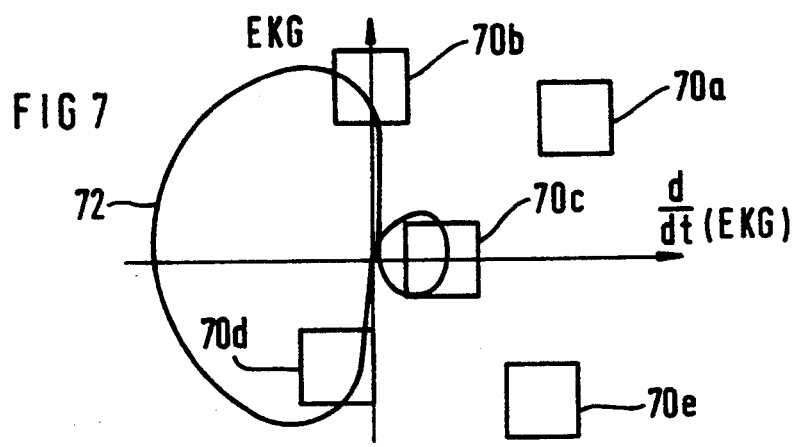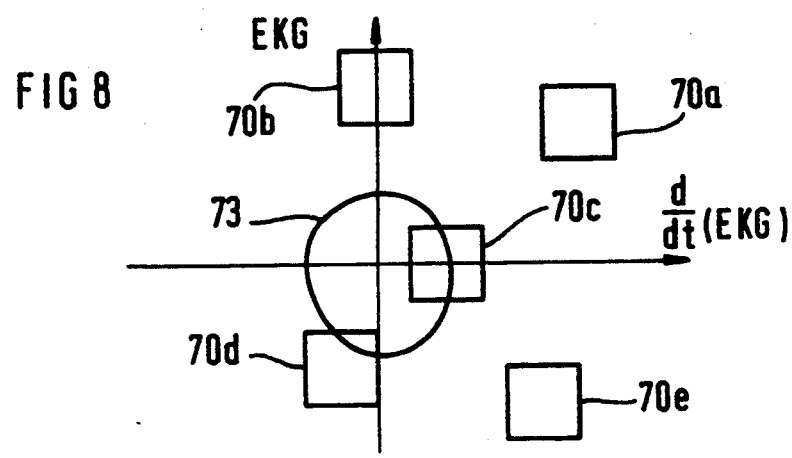

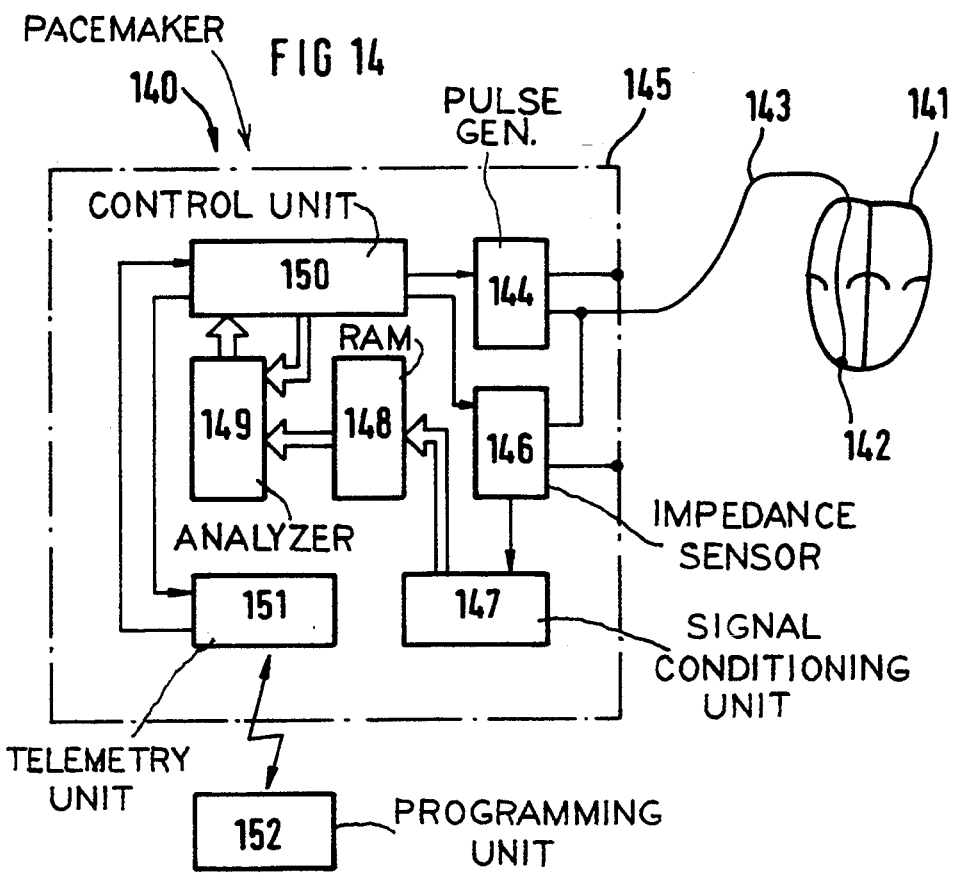
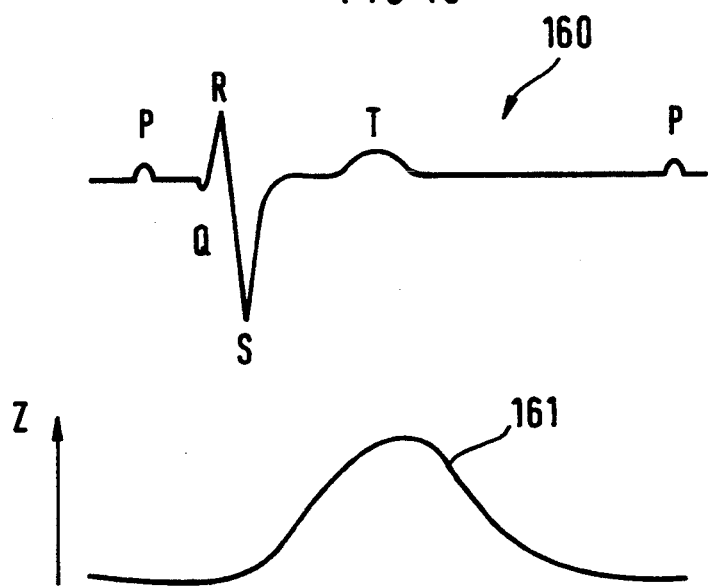

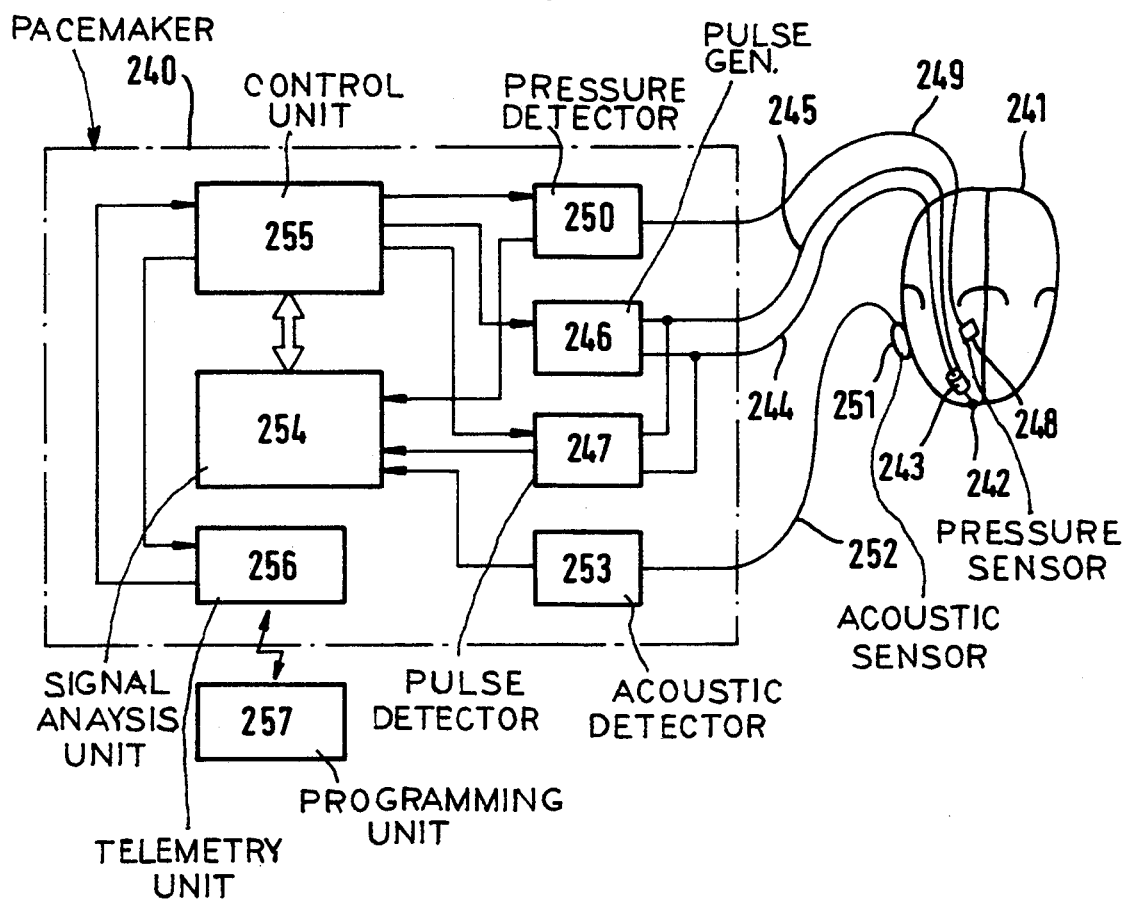

DEVICE FOR ANALYZING THE FUNCTION OF A HEART

BACKGROUND OF THE INVENTION

1. Field of the Invention

The present invention relates to a device for analyzing the function of a heart, having a measurement unit for generating a first measurement signal related to a first electrical or mechanical heart variable, and an evaluation unit for evaluating the measurement signal.

2. Description of the Prior Art

In the monitoring, diagnosis and treatment of heart diseases or other changes in a heart, accurate determination of the heart's current condition, with minimal risk of erroneous interpretations, is important. Automatic monitoring of the heart is valuable so therapeutic measures can be instituted without delay when needed.

There are numerous heart variables, both electrical and mechanical, such as the electrocardiographic (ECG) signal, the heart's impedance, blood pressure, blood volume, blood flow, heart sounds and movements of the heart walls, which reflect the heart's function. The sensing of any of these variables to obtain a measurement signal which can be evaluated in establishing the condition of the heart is known in the art.

One way to graphically elucidate the electrocardiogram by plotting the voltage of a recorded electrocardiogram against the time derivative of the voltage is described in an article 30 entitled "Phase Plane Plot of Electrograms as a Marker of Ventricular Electrical Instability During Acute Ischemia: Initial Experimental Results and Potential Clinical Applications", published in the journal PACE, Vol. 15, Part II, November 1992, pp. 2188-2193. This procedure produces a curve equivalent to the recorded ECG signal. The article shows that there is a relationship between changes in parts of the curve during acute ischemia and development of ventricular fibrillation. The authors of the article state that a presentation of an electrocardiogram in graphical form can be an excellent complement to traditional real-time presentation.

U.S. Pat. No. 4,417,306 describes an apparatus which monitors and stores heart signals. The apparatus senses the ECG, and the ECG signal 5 must have a predetermined slope, amplitude, duration and course to be accepted as a heart beat. The QRS complex is the main segment sensed, i.e. the electrical signals occurring in the heart when there is a ventricular beat (ventricular systole).

U.S. Pat. No. 4,453,551 describes an apparatus designed to detect ventricular fibrillation (VF). The apparatus senses the ECG signal from the heart, digitizes the sensed signal, and amplifies the digital signal to a predetermined peak amplitude. The amplified signal can then be analyzed in different ways to ascertain whether or not VF is present. For example, the statistical distribution of gradients or the frequency of the maximum negative gradient can be analyzed.

European Application 0 220 916 describes an apparatus designed to detect the presence of ventricular tachycardia (VT) and VF and to supply treatment terminating these conditions. The apparatus senses the heart's ECG at a plurality of points in the heart and determines the sequence in which the signals are detected at the different measurement points. In VT and VF, the detected sequence deviates from the normal sequence in different ways.

SUMMARY OF THE INVENTION

It is an object of the present invention is to provide a device which analyzes the function of the heart in a safe, efficient but still simple manner.

Another object of the invention is to provide a device which can be used for diagnosing heart defects, monitoring heart functions and adapting therapy so treatment is as safe and effective as possible.

One such device is achieved in accordance with the principles of the present invention, having a measurement unit and an evaluation unit wherein the evaluation unit further comprises a means for generating a parameter signal related to a heart variable, and wherein the evaluation unit analyzes related values for the measurement signal and the parameter signal.

Instead of analyzing a measurement signal with respect to its characteristics (amplitude, slope, duration), the device analyzes the related values of two signals, i.e., the measurement value and the parameter value are analyzed for the same points in times in the course of the heart variable. In principle, the related values correspond to coordinates in the plane established by the two signals whose changes over time can be analyzed for obtaining information on the condition of the heart. A normally functioning heart is hemodynamically stable, and related values repeat, in principle, from one heart cycle to another. When two conditions must be satisfied simultaneously (the measurement value and parameter value must both be repeated in the same way when heart function is normal), the possibilities of accurately detecting both normal heart function and deviations from normal function increase. Different deviations produce characteristic changes in the signals and can therefore be identified with great accuracy. The measurement signal and parameter signal can be related to the same heart variable. For example, in a pacemaker a unipolar ECG signal can serve as the measurement signal while a bipolar ECG signal can serve as the parameter signal.

An enhancement of the device is obtained in a further embodiment the invention wherein the evaluation unit plots the first measurement signal against the parameter signal and analyzes the morphology and/or chronological course of the curve thus obtained. (As used herein, "morphology" means the shape or structure of the curve, i.e., number of peaks and/or valleys and/or the amplitudes thereof and/or the slope at one or more points and/or regions, whether and where the curve crosses itself, whether it is positive or negative or positive-going or negative-going, enclosed area, etc.).

Such a curve is obtained when the analysis is performed. As noted above, a heart is hemodynamically stable when functioning normally, and a virtually identical curve is generated for each heart cycle, depending on the measurement signal and parameter signal selected. Pathological changes and other anomalies and conditions in the heart affect the shape of the curve in a distinct way and can therefore be easily identified.

Preferably the means for generating a parameter signal are formed by a deriving circuit a derivator which derives a signal from the measurement signal, the derived measurement signal then serving as the parameter signal.

This produces a curve related to only one measured heart variable. For example, a heart's impedance can be plotted against the derivative of that impedance, blood pressure plotted against the derivative of blood pressure or the heart's ECG signal plotted against the derivative of the ECG signal. In the first two instances, substantially circularly shaped curves are obtained whose size depends on e.g., the heart rate. In the latter instance, a curve is obtained consisting of two closed loops per heart cycle at a normal heart rate.

Alternately, the device can be devised so the means for generating a parameter signal senses a second heart variable and generates a second measurement signal serving as the parameter signal.

The plotting of two signals, related to different measured heart variables, against one another, increases the number of possible combinations, and the most suitable curve for identifying a particular disorder, a particular pathological condition or some other change can be selected. For example, pressure can be plotted against impedance, producing a simple, substantially closed curve corresponding to the heart's work in each heart cycle. Infarction can be demonstrated from this curve, since infarction affects the heart's work capacity.

Additional possibilities for identifying different phases of the heart are obtained in a further embodiment of accordance with the invention having a further measurement unit for generating at least one further measurement signal related to at least one further heart variable, whereby the evaluation unit analyzes related values for the first measurement signal, the parameter signal and the further measurement signal.

This produces a multidimensional (non-planar) curve. In principle, any number of heart variables and derivatives of heart variables can be plotted against each other and analyzed. A three-dimensional curve is obtained if impedance is plotted against pressure and the ECG. For every heart cycle, this curve forms a simple closed curve which repeats one heart cycle after another in a healthy heart. An extra or premature ventricular systole would produce a major deviation in the curve. A hemodynamically instable tachyarrhythmia is also easily identified, since the curve is then not repeated in every heart cycle.

In a further embodiment of the invention, a comparator unit continuously senses the related values in order to detect signal drifting by the related values, and a compensation unit compensates the current related values for any current signal drift.

Since heart signals generally display a cyclical course, various types of signal drifting can therefore be compensated. For example, low-frequency, superimposed signals can thereby be eliminated from the actual measurement signal. The device can easily normalize the signals, since they display high repeatability.

Another way of filtering the related values can be undertaken in accordance with the invention, by using a filter unit which, after a first measurement signal and a second measurement signal have been generated, compares changes in the respectively related values to previously stored related values, and noise is identified if a noise change is found in one related value without any equivalent change being found in the second related value, and the noisy related value is compensated by adjusting for the specific noise therein.

For example, ECG signals and impedance signal are affected by certain types of noise caused by, e.g., patient breathing. One heart variable, such as blood pressure, however, is not affected by noise in the same way as purely electrical heart signals and can therefore be used for identifying noise in the electrical signals and vice-versa.

Yet another way of filtering a signal with the aid of the device is achieved in accordance with the invention by using a floating averager which continuously calculates the average value for the respective related value over a predetermined previous period of time.

Many advantageous specific embodiments of the device for analyzing related values are possible according to the present invention, some of which will be described below in greater detail.

In a first embodiment, the evaluation unit is an arc length calculator which calculates the arc length of the curve, preferably for one heart cycle, the calculated arc length value then designating the condition of the heart's function.

For certain measurement signal-parameter signal pairs (e.g., impedance and the derivative of impedance), the arc length of the curve for every heart cycle corresponds to prevailing hemodynamic stability, making it easy to establish from the arc length whether the heart is beating at an innocuous rate or if the heart is displaying unstable bradycardia or tachyarrhythmia. If the change in arc length from one heart cycle to another is recorded, hemodynamic stability can be identified and employed as a sub-condition of the rate in determining whether an unstable arrhythmia is present. Rapid changes are indicative of abnormal events in the heart.

In this first embodiment, preferably the measurement unit measures impedance in the heart, the means for generating a parameter signal differentiates the impedance signal, an A/D converter digitizes the impedance signal and the impedance derivative signal, the arc length calculator calculates the arc length for each heart cycle of the curve to which the impedance signal and the impedance derivative signal correspond, a number of comparators respectively compare the calculated arc length to a predetermined arc length, each comparator then generating an output signal if the calculated arc length exceeds the respective predetermined arc length, and a microprocessor, using the output signals from the comparators, determines whether the heart is hemodynamically stable.

Different hearts vary in their ability to withstand high rates, but the most important physiological condition is whether the heart is hemodynamically stable, i.e., whether it pumps blood in a normal manner, thus heart rate does not always constitute the best indicator of the condition of the heart. For example, some patients may have problems at a heart rate of 150 beats/min, whereas other patients might be able to withstand more than 200 beats/min without any impairment in the pumping capacity of their hearts. During the heart cycle, impedance changes in such a way that it rises during systole when blood is pumped out of the heart and falls during diastole when the heart fills with blood. The change in impedance is more rapid at the beginning of systole and the beginning of diastole respectively, as reflected in their differentiated signals. In a coordinate system, impedance and differentiated impedance signals form a closed curve for each heart cycle, and the arc length only varies only within certain limits as long as the heart is hemodynamically stable. When the heart is no longer able to function in a hemodynamically stable fashion, the arc length declines, something easily detected by a comparator. Depending on the different output signals from the comparators, the heart's hemodynamic condition can therefore be continuously monitored. This would not be possible if e.g., only the heart rate or the peak-to-peak value for impedance, which do not vary as systematically as the arc length in the presence of hemodynamic instability, were considered.

In a second embodiment, the evaluation unit is an area calculator which calculates an area, substantially enclosed by the curve, for every heart cycle, the calculated area then designating the condition of the heart's function.

Area is related to hemodynamic stability in the same way as arc length for certain measurement signal-parameter signal pairs, and can be used in the same way as arc length for identifying unstable arrhythmias. For other measurement signal-parameter signal pairs (pressure and impedance or volume and pressure), area represents the work performed by the heart in each heart cycle, and this can be used for controlling an atrio-ventricular interval in a dual chamber pacemaker so that optimum functioning of the heart is attained for the heart or for controlling the emission of stimulation pulses in a way which optimizes the heart's work.

In a third embodiment, the evaluation unit plots a simple, closed curve and a distance calculator calculates the distance between specific points on the curve, preferably between maximum and minimum points, the calculated distances designating the condition of the heart's function.

In the same way as for arc length and area, the distances between points on the curve for certain measurement signals and parameter signals represent the stability of the heart. The ratio between certain distances, such as the distance between the maximum and minimum points on the curve for the respective coordinate axis, can be established. Variations in the distance can be calculated and utilized for e.g., determining the heart's work. With, e.g., blood pressure in the heart as a variable, conditions in which the heart's pumping capacity declines can be easily identified, since pressure changes during a heart cycle then decline.

In a fourth embodiment, the evaluation unit is a memory for storing the obtained curve for each heart cycle and a comparator for comparing the obtained curve with at least one predetermined curve, the predetermined curve being either a previously stored curve or a programmed curve.

In this manner, the morphology of each heart cycle can be directly compared with morphologies in normal hearts and with pathological conditions or other anomalies. For example, mild infarctions sustained by the heart, extrasystoles and retrograde conduction can be detected.

In a fifth embodiment, the evaluation unit ia a memory for storing the course of related values, and a comparator for comparing the stored course with at least one predetermined course, the predetermined course being either a previously stored course or a programmed course.

As previously noted, the related values follow a course which essentially repeats from one heart cycle to another. Different conditions can be identified if this course is monitored. The course can be monitored, e.g., by regarding related values as calculating gradients from changes in related values. For example, distinctions can thereby be made between different forms of arrhythmias arising from different foci in heart tissue, and both old and new conditions suffered by the patient can also be detected. Different therapies can be provided, depending on the therapy previously found to be effective for the various arrhythmias.

In this context, preferably the device comprises a component for identifying a sequence with which the course of related values passes a predetermined number of areas and the comparator compares the sequence to a predetermined sequence, the predetermined sequence being either a previously identified sequence or a programmed sequence.

Since the related values repeat, sensing only certain areas traversed by the values and identifying that sequence, or possibly even the time interval between the different areas, is sufficient. Different arrhythmias follow different paths and can also be identified in the corresponding manner. Such a device is in U.S. application Ser. No. 08/051,249 simultaneously filed herewith.

DESCRIPTION OF THE DRAWINGS

FIG. 5 shows a block diagram of a second embodiment of the device, used in a pacemaker.

FIGS. 6–8 respectively illustrate in the form of coordinate system diagrams the function of the second embodiment.

FIG. 14 shows in form of a block diagram a fifth embodiment of the device, used in a rate-responsive pacemaker.

FIG. 15 shows how impedance in the heart varies during a heart cycle.

FIG. 22 shows a block diagram of a tenth embodiment of the device, used in a pacemaker.

DESCRIPTION OF THE PREFERRED EMBODIMENTS

Figure 1:
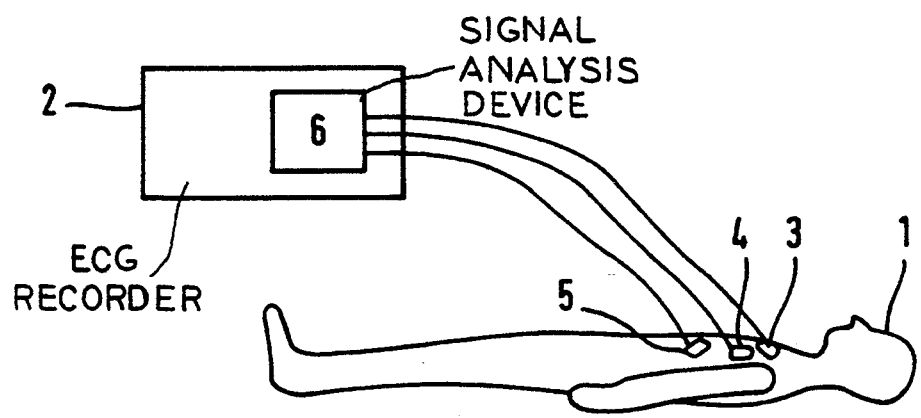
FIG. 1 shows a first embodiment of the device in accordance with the invention, used in an ECG apparatus.

FIG. 1 shows a patient 1 connected to an ECG recorder 2 via a first electrode 3, a second electrode 4 and a third electrode 5. The patient's 1 ECG signal may be sensed in a routine examination of the patient's health, for diagnosis of a suspected heart condition or for monitoring of the heart of the patient 1. A signal analysis device 6 is constructed in accordance with the principles of the present invention is provided in the ECG recorder 2 to analyze the ECG signals picked up by the electrodes 3, 4 and 5.

Figure 2:
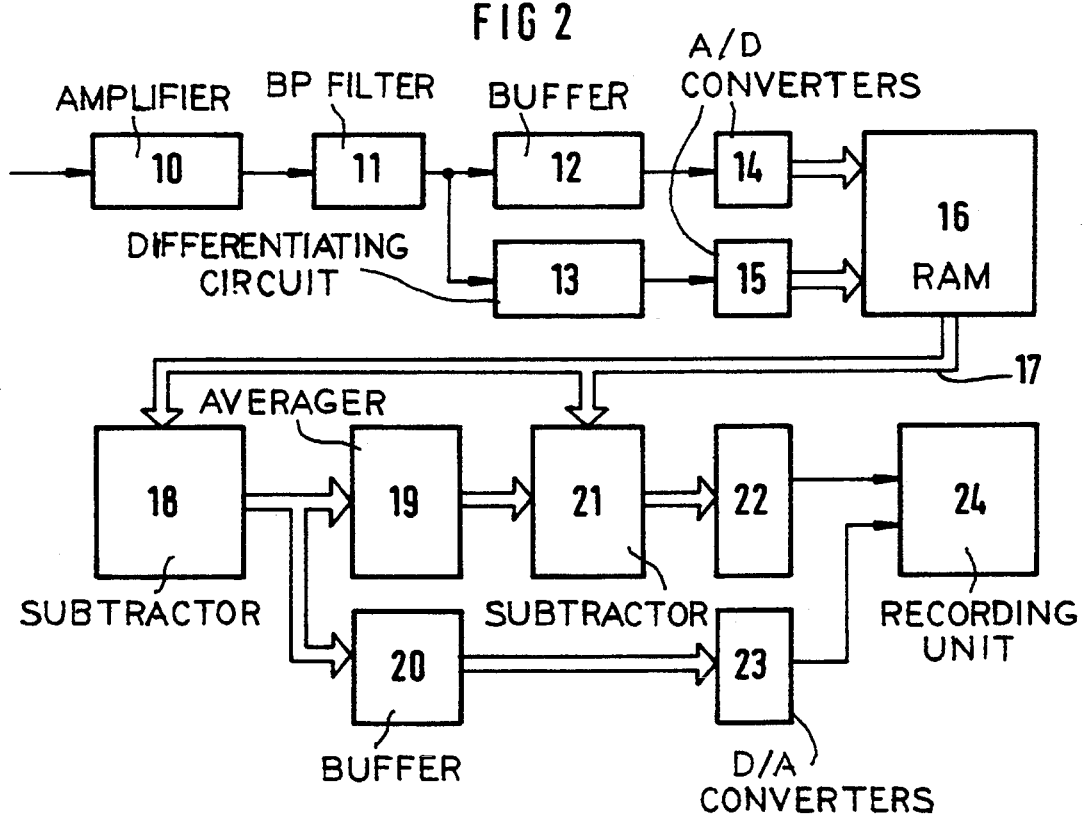
FIG. 2 shows the first embodiment in the form of a block diagram.

FIG. 2 shows an embodiment of the signal analysis device 6. The ECG signal is fed into an amplifier 10 and then filtered in a bandpass filter 11 before the signal is transferred to a differentiating circuit 13 and to a buffer 12 in which it is chronologically synchronized with the differentiated signal. The signal in the buffer 12 and the differentiated signal are then transferred, via a first A/D converter 14 and a second A/D converter 15 respectively to a RAM 16. Related values for the two input signals are stored in parallel in the RAM 16. The related values are chronologically simultaneous signals. The digitized signals then pass from the RAM 16, via a data bus 17, to a first subtractor 18 in which current measurement values are subtracted from a basic signal. The basic signal can consist of a previously recorded and stored ECG signal from the same patient. Differences can be calculated for entire heart cycles or parts of heart cycles, primarily depending on the heart rate and noise frequencies. Difference values are then fed to an averager 19 which calculates an average value for the difference. The difference is also fed to a signal buffer 20 for subsequent use as a diagnostic aid. The averaged signal is sent to a second subtractor 21, to which the original signal is also sent, in order to compensate it for noise in the recorded ECG signal. From the second subtractor 21 the signal passes a first D/A converter 22 and the difference signal is fed to a second D/A converter 23 from the signal buffer 20. Both signals are now fed to a recording unit 24 which can consist of a recorder, monitor or the like.

Figure 3:
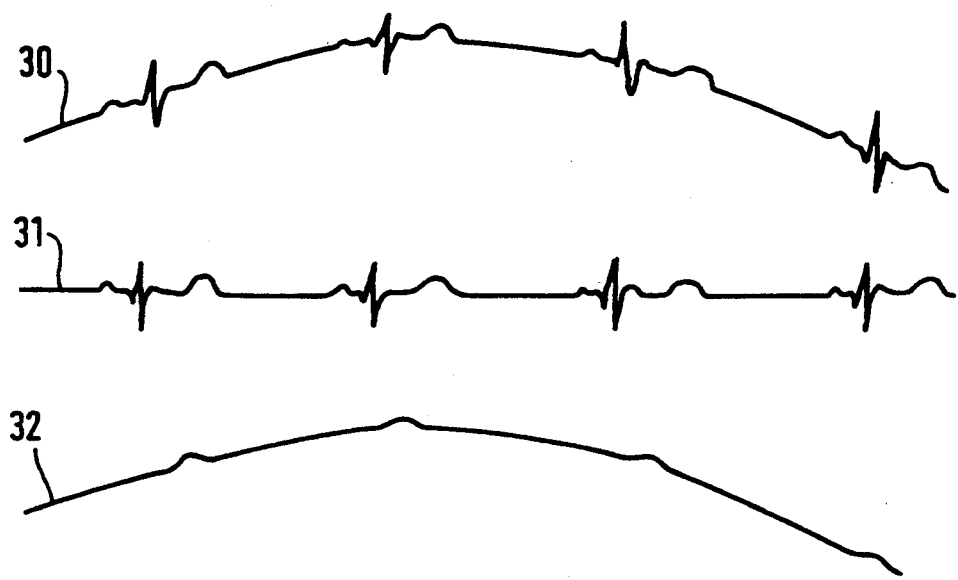
FIG. 3 shows a diagram for describing the function of the first embodiment.

The ECG signal before and after signal conditioning is illustrated in FIG. 3 in which the recorded ECG signal is designated 30. The recorded ECG signal 30 has a superimposed noise signal with a lower frequency, making interpretation of heart signals more difficult. In the signal analysis device 6, as described in FIG. 2, the ECG recorded signal 30 is normalized in relation to a previously stored, correct ECG signal, and the ECG signal is compensated for the distortion caused by signal noise by subtraction of the noise from that ECG signal 30. The conditioned ECG signal, designated 31, is much more distinct and much easier for the physician to interpret. In principle, the difference signal 32 produced in the signal analyzer reflects the noise. Noise can be caused e.g., by breathing of the patient 1, so the difference signal 32 can also be used for recording the breathing of the patient 1. Deviations in the recorded ECG signal 30 from the stored basic signal also appear in the difference signal. These changes may be due to changes in the heart, such as infarction, ischemia or late potentials.

Figure 4:
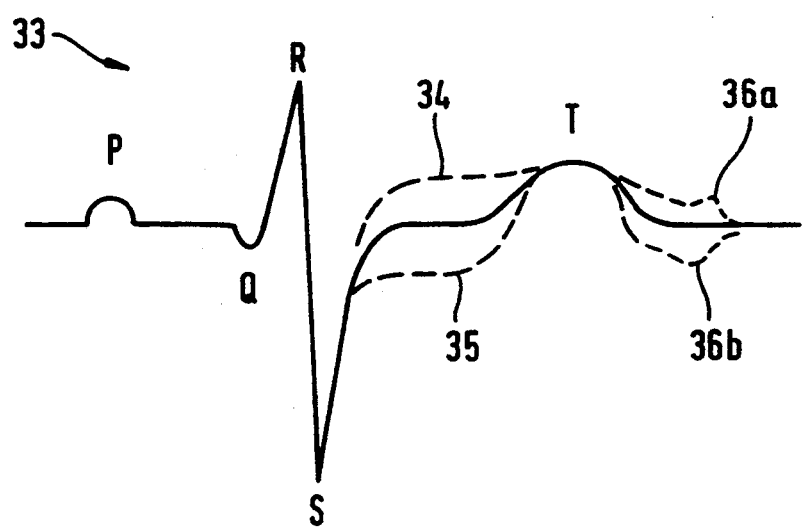
FIG. 4 shows an ECG for one heart cycle.

The morphology of a heart signal is shown in FIG. 4 and generally designated 33. The heart signal 33 consists of a P wave caused by atrial depolarization (which starts atrial systole), a QRS wave caused by ventricular depolarization (which starts ventricular systole) and a T wave caused by ventricular repolarization. Pathological and other changes in the heart affect the heart signal 33 in characteristic ways. An elevation of the signal such as that designated 34 in the S wave and the T wave is generally caused by infarction in the heart, such an infarction impairing the heart's work capacity. On the other hand, depression of the signal such as that designated 35 between the S wave and the T wave is generally caused by ischemia, i.e., inadequate blood perfusion in local areas of the heart, leading to hypoxia in the heart. One of the most common causes of cardiac ischemia is arteriosclerosis. Changes at the end of the T wave, here designated 36a and 36b in the heart signal 33, are generally interpreted as changes increasing the risk of tachycardia or fibrillation, compared to other hearts. Such a change may be a sign that the patient needs treatment with medication or an implantable defibrillator.

FIG. 5 shows an implantable dual chamber pacemaker 40 which is connected to a heart 41 to sense the heart's ECG and deliver treatment when necessary. The pacemaker is connected to the heart 41 with a first tip electrode 42 and a first ring electrode 43. The first tip electrode 42 and the first ring electrode 43 are connected, via a first electrode conductor 44 and a second electrode conductor 45, to an atrial pulse generator 46. An atrial detector 47 is connected in parallel across the pulse generator 46 to sense the ECG signal of the heart 41.

In the corresponding manner, a second tip electrode 48 and a second ring electrode 49 are connected, via a third electrode conductor 50 and a fourth electrode conductor 51, to a ventricular pulse generator 52. A ventricular detector 53 is connected across the ventricular pulse generator 52 to sense the ECG signal of the heart 41. The pulse generators 46 and 52 and the detectors 47 and 53 are controlled by a control unit 54.

The ECG signals picked up by the detectors 47 and 53 are fed to a signal conditioning unit 55 in the control unit 54. The input signals are processed in the signal conditioning unit 55 in the same was as shown in FIG. 2, i.e., with gain, filtration, buffering and derivation and A/D conversion. The digitized signals are transferred to a RAM 56 which sequentially stores the related values. In principle, stored values correspond to coordinates in a coordinate system which has the ECG signal as one axis and the derived ECG signal as the other axis. The stored related values form a curve in this coordinate system. The related values are sent from the RAM 56 to an area analyzer 57. The area analyzer 57 senses whether curve of the related values passes through specific areas in the coordinate system. Data regarding on the areas traversed and the sequence in which they are traversed are transferred to a sequence identifier 58 which compares the sequence previously stored or programmed sequences. Sequence information is sent from the sequence identifier 58 to a therapy selection unit 59. On the basis of this transmitted information, the therapy selection unit 59 decides whether therapy should be instituted. If the sensed sequence of related values results in a sequence which is not stored in the sequence identifier 58, this sequence is sent from the RAM 56 to an extra memory 60, from which it can then be retrieved and studied by a physician.

To permit the pacemaker 40 to transmit information about new sequences or to accept programming, the pacemaker 40 is equipped with a telemetry unit 61 connected to the therapy selection unit 59 which includes programmable control circuitry in addition to the "decision making" circuitry. The telemetry unit 61 can telemetrically transmit information between the control unit 59 and an extracorporeal programming unit 62.

The analysis of the ECG signal which takes place in the pacemaker 40 is illustrated in greater detail in FIGS. 6, 7 and 8 which show different heart signals in a coordinate system with the ECG signal and the derivative of the ECG signal as axes. Five analysis areas 70a through 70e are designated in the three FIGS. 6, 7 and 8. FIG. 6 shows a curve 71 for a normal heart beat. This curve 71 traverses all five analysis areas 70a through 70e in a specific sequence and can therefore be easily identified as a natural event by the pacemaker 40. FIG. 7 shows a tachyarrhythmia curve 72 at about 150 pulses/minute. The tachyarrhythmia curve 72 only passes three analysis areas 70b, 70d and 70c and is therefore very easy to identify. A tachyarrhythmia can originate at various foci in heart tissue, and each specific type of tachyarrhythmia can be identified in this way according to the sequence in which the curve passes the analysis areas 70a through 70e. This is particularly important, since the most effective termination of different tachyarrhythmias can require different therapeutic stimulation sequences. In addition, certain tachyarrhythmias are hemodynamically stable, i.e., do not require any therapeutic intervention, whereas other tachyarrhythmias spontaneously subside after a time and do not require any treatment either. In the case of unstable tachyarrhythmias, the control unit 59 can be programmed with a plurality of different therapeutic pulse rates and, depending on the tachyarrhythmia detected, deliver the therapeutic measure which has proved to be most effective for that type of tachyarrhythmia. FIG. 8 illustrates a heart fibrillation 73 which only results in a small, simple, closed ring which traverses two analysis areas 70c and 70d in this instance. Defibrillation of the heart 41 can be necessary when fibrillation occurs. An implantable defibrillator could be used to deliver such therapy, which may also include the pacemaker functions.

Figure 9:
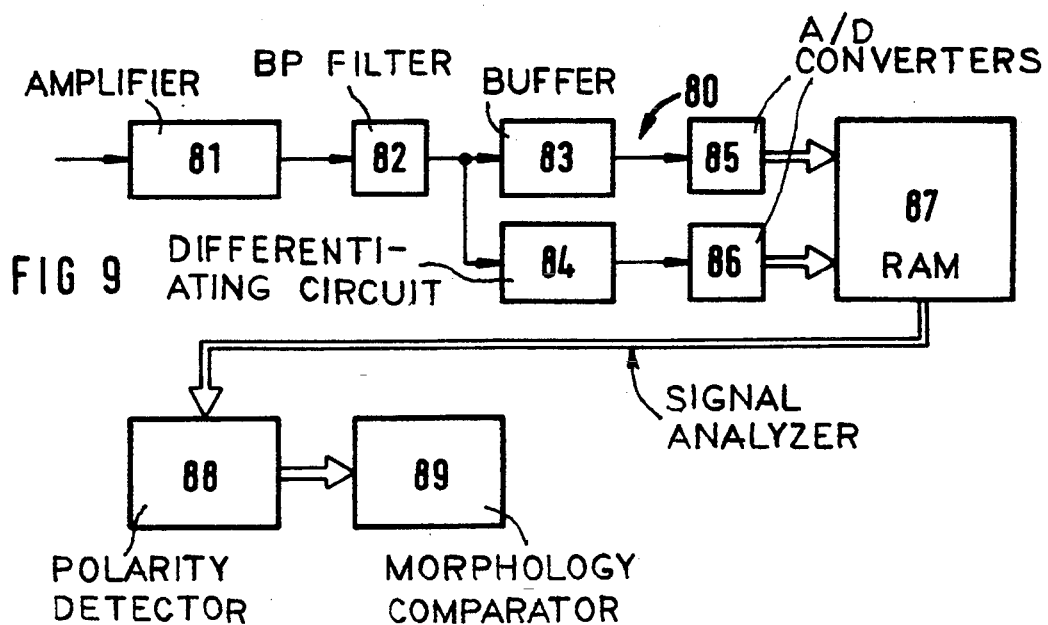
FIG. 9 shows a block diagram of a third embodiment of the device, used in a pacemaker.

FIG. 9 shows an alternative embodiment of the device according to the invention. A signal analyzer 80 amplifies an ECG signal in an amplifier 81 and filters the amplified signal in a bandpass filter 82 before the signal is fed to a buffer 83 and to a differentiating circuit 84 in which a derived signal is obtained, such as by differentiation.

The buffered signal and the derived signal are respectively digitized in a first A/D converter 85 and a second A/D converter 86 and are fed therefrom to a cyclical RAM 87. Since both the ECG signal and its derivative is used, simple signal normalization can be performed in the cyclical RAM 87.

The signals are then fed to a polarity detector 88 which senses whether the derived signal is positive or negative. For each heart cycle, a sequence of changes in the derivative during the heart cycle is sent to a morphology comparator 89. The morphology comparator 89 compares this sequence with previously generated sequences and identifies the current condition of the heart, e.g., whether it is functioning normally, whether it is responding to stimulation pulses, whether it is in arrhythmia, etc.

Figure 10:
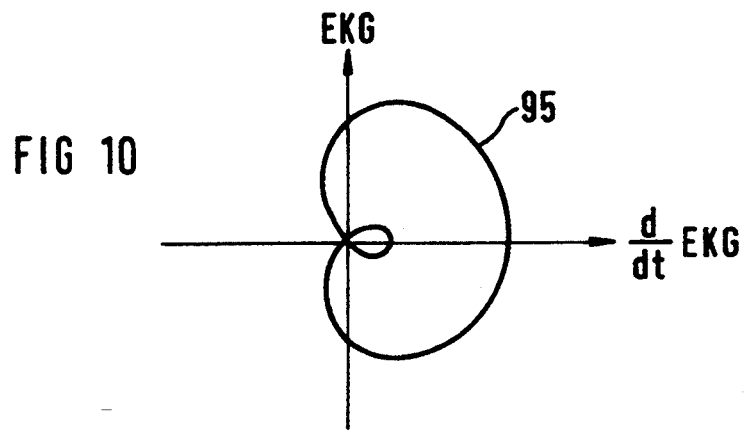
FIGS. 10–11 respectively illustrate in the form of coordinate system diagrams the function of the third embodiment.
Figure 11:
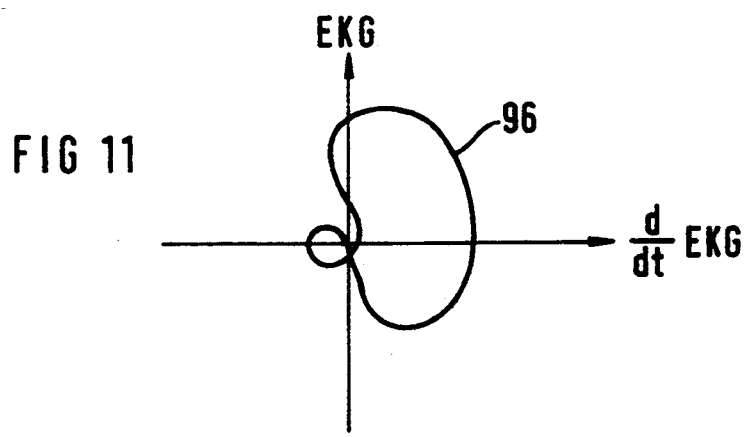

Two different heart rhythms are illustrated in FIGS. 10 and 11. A first ECG-ECG derivative tracing 95 is shown in FIG. 10. This first tracing 95 has a typical, readily identifiable sequence of alternating positive and negative derivatives whose respective arc lengths can be obtained, e.g., in the form of a number of sampled values with positive or negative derivatives. A second ECG-ECG derivative tracing 96, shown in FIG. 11, has a different sequence of positive and negative derivatives with other arc lengths under the positive and negative segments respectively. In the individual patient, each heart condition (normal function, stable tachyarrhythmia, unstable tachyarrhythmia, fibrillation etc.) has a characteristic, recurrent sequence of positive and negative derivatives with specific arc lengths. The signal analyzer 80 can be programmed to acquire the different sequences occurring in a patient, and to store those sequences for retrieval by a physician who can then get a good picture of the heart's condition and function.

Another criterion which can be employed in improving reliability in the identification of a specific condition is the ECG signal itself (positive, negative, arc length).

As noted above, it is easy for the signal analyzer 80 to normalize the signal which, in contrast to analyzers which only examine the derivative signal, results in easy attainment of a zero level for the derivative on a stable level, i.e., conditioning of the ECG derivative signal readily compensates for signal drifting, making the analysis more reliable.

Figure 12:
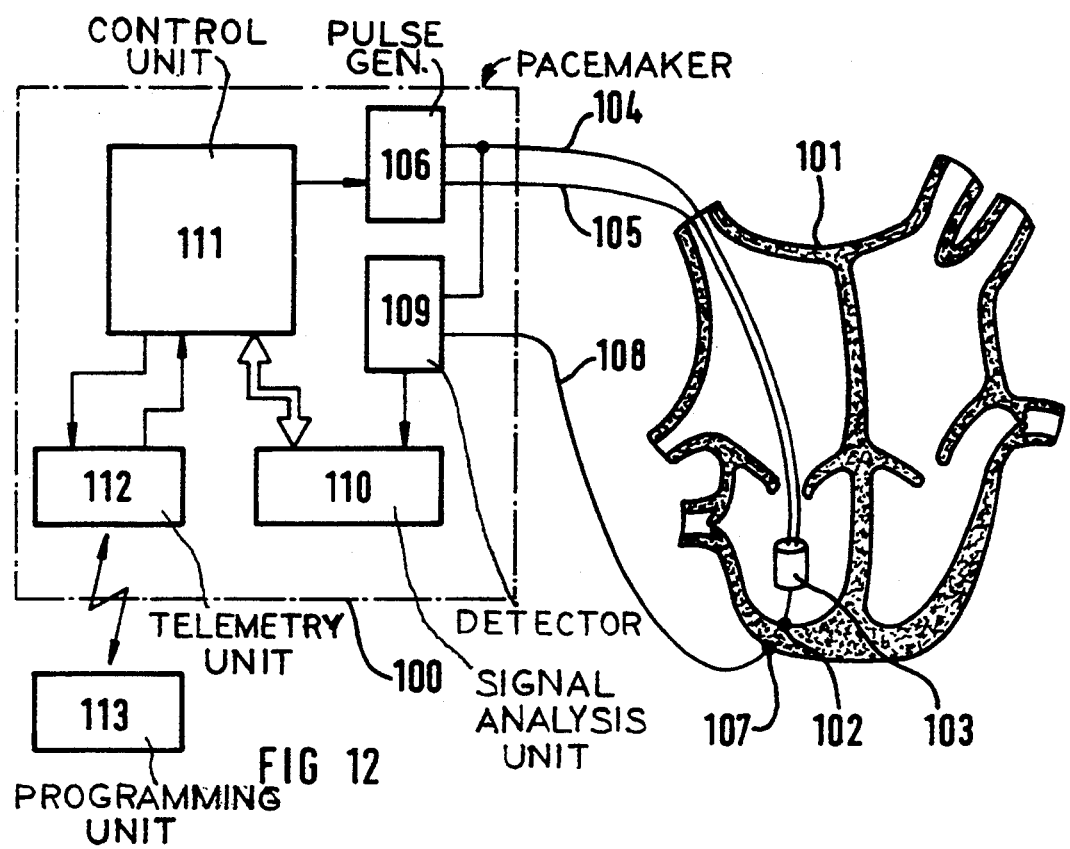
FIG. 12 shows a block diagram of a fourth embodiment of the device, used in a pacemaker.

FIG. 12 shows a single chamber pacemaker 100 which is connected to a heart 101. A tip electrode 102 and a ring electrode 103 are placed in the ventricle of the heart 101 and connected, via a first electrode conductor 104 and a second electrode conductor 105, to a pulse generator 106 in the pacemaker 100. A detector electrode 107 is connected to the exterior of the heart near the tip electrode 102 and, via a third electrode conductor 108, to a detector 109 in the pacemaker 100. The detector 109 senses the impedance of the heart wall between the tip electrode 102 and the detector electrode 107 and transfers this signal to a signal analysis unit 110 which is described in greater detail in FIG. 13. Results of the signal analysis are sent to a control unit 111 which, according to the impedance signal analyzed by the signal analysis unit 110, controls the pulse generator 106.

As in the previously described pacemakers, this pacemaker contains a telemetry unit 112 which transmits information between the control device and an extracorporeal programming unit 113.

Figure 13:
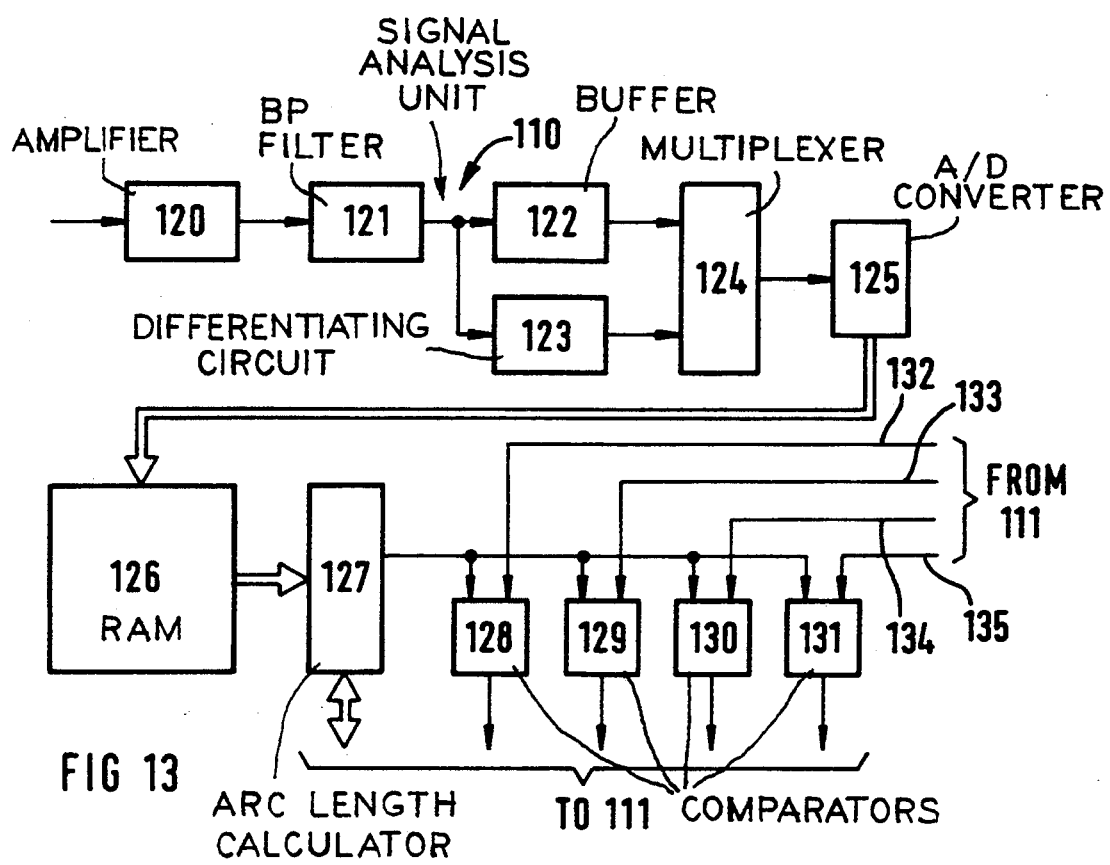
FIG. 13 shows the fourth embodiment in a more detailed block diagram.

In the signal analysis unit 110, as shown in FIG. 13, the impedance signal first passes an amplifier 120 and a bandpass filter 121 before the signal is split into two parts. The first part goes to a buffer 122 and the second part goes to a differentiating circuit 123. From the buffer 122 and the differentiating circuit 123 the signals are respectively multiplexed in a multiplexer 124, fed to an A/D converter 125 and then stored in a RAM 126. From the RAM 126 the related values are sent to an arc length calculator 127 which calculates the arc length of the curve which impedance and the derivative of impedance form in a coordinate system with impedance and the derivative of impedance as coordinate axes. The arc length calculator 127 suitably calculates the arc length for each individual heart cycle. The measured arc length is then transferred to a first comparator 128, a second comparator 129, a third comparator 130 and a fourth comparator 131 for comparison to previously stored or programmed arc lengths. The values to be compared to the current arc length are transferred from the control device 111 via a first signal conductor 132, a second signal conductor 133, a third signal conductor 134 and a fourth signal conductor 135. The comparators 128, 129, 130 and 131 are each devised to emit a signal only if the currently measured arc length exceeds the arc length to which it is compared. The control device 111 utilizes the time interval between the signals from comparators 128 through 131 as a sub-condition in the analysis. This means that the output signal from the four comparators 128, 129, 130 and 131 which are transferred to the control device 111 can designate five different arc length intervals which, with the time intervals, can be analyzed by the control device 111. The first occurs when the current arc length is shorter than all the arc lengths to which it is compared. The output signal from the comparators 128 through 131 is then low (i.e., a "zero") which means that the heart has a hemodynamically unstable tachyarrhythmia if the time interval is short and hemodynamically unstable bradycardia if the time interval is long. The second situation occurs when the current arc length is only longer than one of the arc lengths to which it is compared, e.g., the length sent to the comparator 131 via the signal conductor 135, which is indicative of, e.g., a fast heart rate on the verge of hemodynamic instability if the time interval is simultaneously short. The third situation occurs when the current arc length is longer than two of the arc lengths to which it is compared, e.g., comparator 130 and comparator 131 each produce high output signals (i.e, a "one"). This could correspond, e.g., to a normal, stable heart rate between approximately 80–120 pulses/minute. The fourth situation occurs when the current arc length is longer than three of the arc lengths to which it is compared, e.g., comparator 129, comparator 130 and comparator 131 all produce high output signals. This may correspond to a slow rate on the verge of stability if the time interval is simultaneously long. Finally, the fifth situation occurs when the arc length is longer than all the other arc lengths to which it is compared, i.e., all the comparators 128, 129, 130 and 131 produce high output signals. If the time interval is simultaneously long, this is indicative of bradycardia in a heart whose pumping capacity is greatly diminished, i.e., a hemodynamically unstable heart. The control unit 111 can, on the basis of the signals from the comparators 128, 129, 130 and 131, thus determine whether the heart is stable.

It should be noted that the derivative of the signal need not be established explicitly, but can be estimated by sampling the signal values and having the difference between two sampled value correspond to the derivative. With an adequate sampling frequency and relatively "well-behaved" curves, the estimated value for the derivative will suffice for analysis.

FIG. 14 shows a unipolar single chamber pacemaker 140 connected to a heart 141. A tip electrode 142 is placed in the right ventricle of the heart 141 and connected, via an electrode conductor 143, to a pulse generator 144. A stimulation pulse from the pulse generator 144 is fed to the heart via the electrode conductor 143 and the tip electrode 142 and is returned to the heart 141 through body tissue, the pacemaker can 145 and back to the pulse generator 144. An impedance sensor 146, also connected to the pacemaker can 145, is also connected to the electrode conductor 143 for measuring impedance across the chest, the impedance of the heart extractable therefrom through filtration.

The measured impedance is sent to a signal conditioning unit 147 in which the signal is amplified, filtered, buffered and derived in the same way as previously described, and digitized. The digitized signals are transferred to a sequential RAM 148 and then to an analyzer 149, whose function is described in greater detail below in conjunction with FIG. 16. A control unit 150 controls the pulse generator 144 and the impedance sensor 146.

Via a telemetry unit 151, using a programming unit 152, a physician can communicate with the pacemaker 140.

An impedance signal 161 is shown in FIG. 15 with an ECG tracing 160 to illustrate the way in which impedance varies during a heart cycle.

Figure 16:
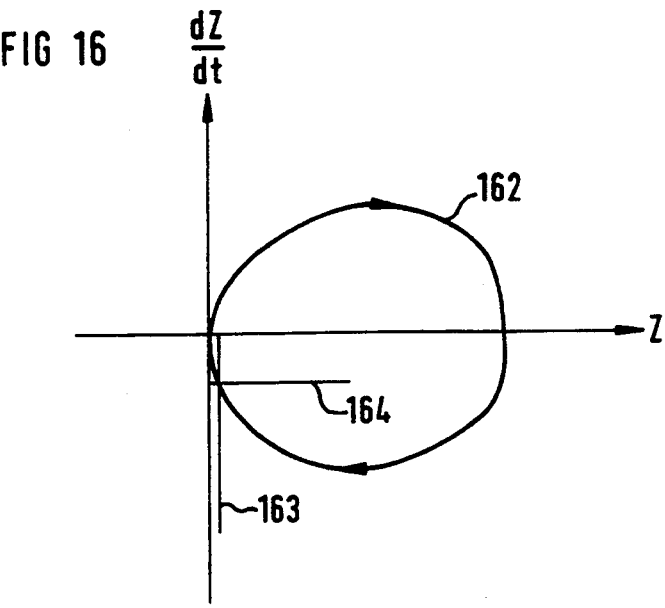
FIG. 16 illustrates in the form of a coordinate system diagram the function of the fifth embodiment.

In FIG. 16, the impedance signal and its derived signal have been plotted in a coordinate system with impedance Z as one axis and the derivative dZ/dt as the other axis. The plotted impedance signal and impedance derivative signal 162 form a simple, closed curve for each heart cycle. The zero impedance level has been placed at the lowest value of the impedance signal 161. The upper part of the derivative axis, i.e. the positive derivative, corresponds to systole, i.e., the contraction phase of the heart cycle, and the negative derivative corresponds to diastole, i.e., the blood filling phase. In principle, it is this impedance signal and impedance derivative signal 162 which are stored in the RAM 148 in FIG. 14.

The impedance signal and impedance derivative signal 162 are used by the analyzer 149 for monitoring and controlling the emission of stimulation pulses to the heart. Here, there are different types of threshold values the analyzer can sense in establishing the time for emission of a stimulation pulse. For example, a threshold value 163 can be set for the impedance, whereby a stimulation pulse is emitted when the impedance signal exceeds the threshold value 163 during diastole. Another way is to set the threshold value at a particular derivative value 164 which the negative derivative must exceed during its ascent at the end of diastole. Alternately, both conditions can be used, i.e., the vector (Z, dZ/dt) is determined and a stimulation pulse emitted when the vector is shorter than a given value.

Another way of controlling the emission of stimulation pulses is based on optimization of the area covered by the impedance and impedance derivative signal 162 in each heart cycle. This can be accomplished, e.g., by maximizing the expression:

$$|Z_{max}-Z_{min}| \cdot |[dZ/dt]_{max}-[dZ/dt]_{min}|.$$

Figure 17:
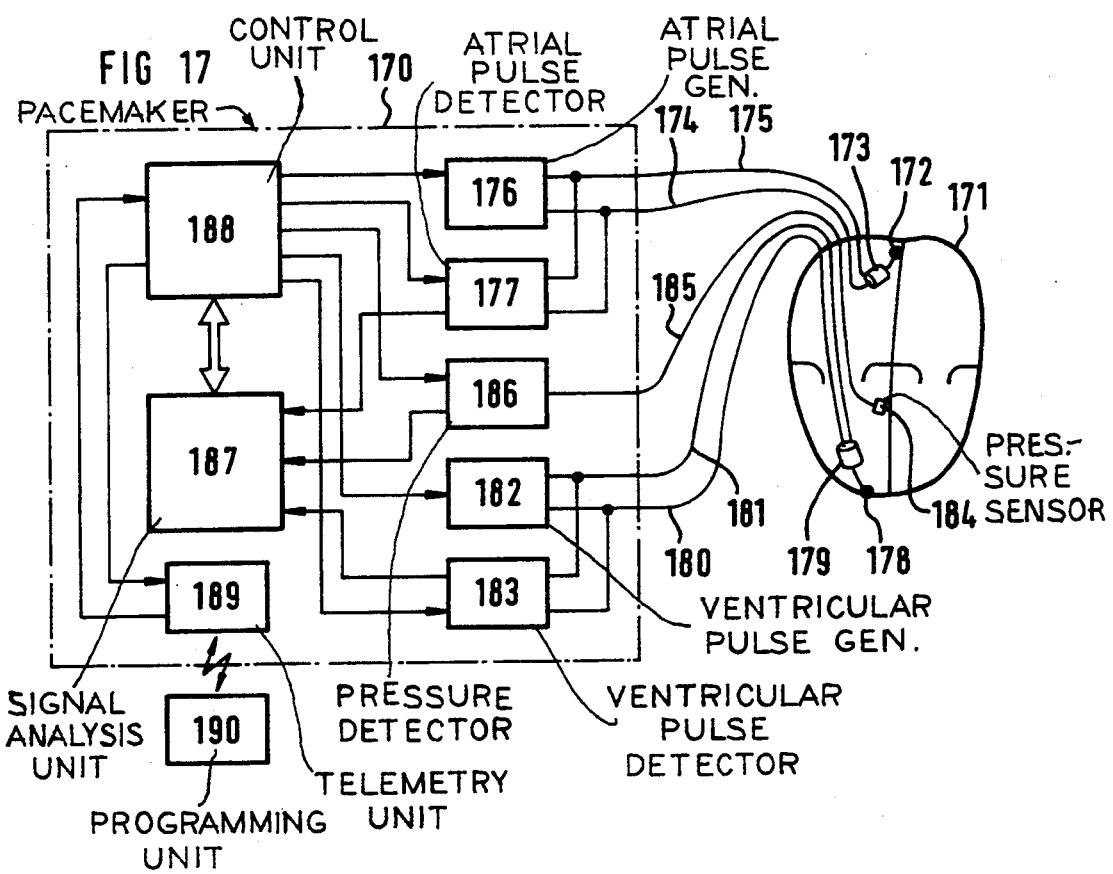
FIG. 17 shows a block diagram of a sixth embodiment of the device, used in a rate-responsive pacemaker.

FIG. 17 shows an additional embodiment of the invention in the form of a pacemaker 170 connected to a heart 171. As in the previously described dual-chamber pacemakers, this pacemaker is also connected to the heart by a first tip electrode 172 and a first ring electrode 173 which, via a first electrode conductor 174 and a second electrode conductor 175, is connected to an atrial pulse generator 176. An atrial detector 177 is connected in parallel across the atrial pulse generator 176. The atrial detector 177 can, e.g., sense ECG signals or sense the impedance between the first tip electrode 172 and the first ring electrode 173.

A second tip electrode 178 and a second ring electrode 179 are placed in the ventricle of the heart 171 and connected, via a third electrode conductor 180 and a fourth electrode conductor 181 to a ventricular pulse generator 182 in the pacemaker 170. A ventricular detector 183 is connected in parallel across the ventricular pulse generator 182.

In this embodiment, a pressure sensor 184 has also been introduced into the ventricle to sense ventricular blood pressure. The pressure sensor 184 is connected, via a signal conductor 185, to a pressure detector 186. The measurement values sensed by the detectors 177, 183 and 186 are sent to a signal analysis unit 187 for conditioning and evaluation. A control unit 188 communicates with the signal analysis unit 187 and also controls the pulse generators 176, 182 and the detectors 177, 183 and 186. Via a telemetry unit, a physician can retrieve and program information to/from the pacemaker 170 with a programming unit 190.

Figure 18:
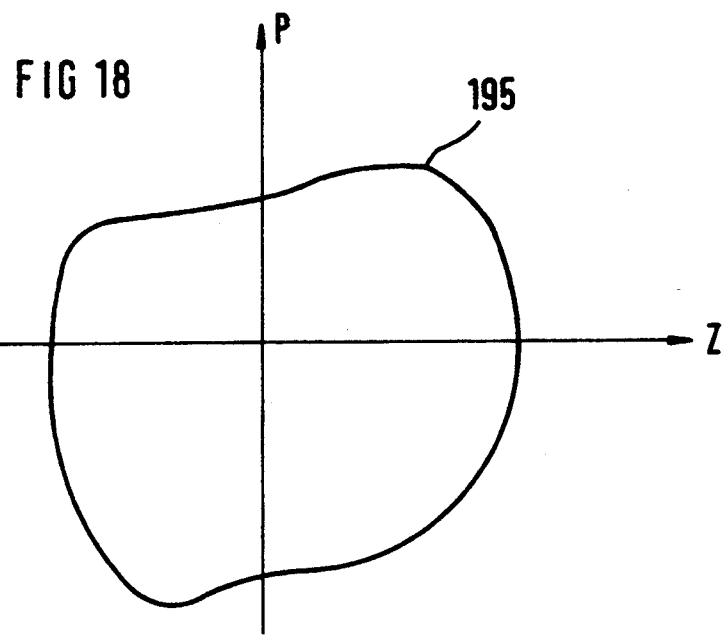
FIG. 18 illustrates in the form of a coordinate system diagram the function of the sixth embodiment.

When, e.g., impedance is measured in addition to pressure, an impedance-pressure curve 195 is obtained, as shown in FIG. 18 in the impedance-pressure coordinate system drawn there. The zero level for the impedance part of the curve 195 has been placed on a different level from the impedance signal in FIG. 16. The closed, simple impedance-pressure curve 195 corresponds to one heart cycle. Impedance is generally unchanged at the end of diastole, whereas pressure rises because the ventricle is incapable of admitting more blood. During systole, initial pressure rapidly increases until the valves between the heart and the vascular system open, pressure is then substantially constant while impedance increases because of the expulsion of blood. Peak pressure occurs during systole at the same time as impedance rises to a peak. Since heart muscle generally relaxes at the end of systole and blood again flows into the heart, pressure rapidly drops while impedance begins falling again.

By maximizing the area enclosed by the impedance-pressure curve 195, the pacemaker can be controlled in the same way as the pacemaker in FIG. 14. The impedance-pressure signal 195 can also be used for detecting or verifying a tachyarrhythmia or fibrillation, since the heart's pumping capacity virtually disappears under those conditions, even if the ECG signal can still look normal. The impedance-pressure signal 195 is then compressed, virtually into a line parallel to the impedance axis Z, on the pressure axis. The impedance-pressure signal 195 can also be used for determining the duration of different periods in the heart signal, e.g., the heart's isovolumetric relaxation phase or the heart's isovolumetric contraction phase. The latter corresponds to the preejection period (PEP) used as a parameter in the rate control of pacemakers. Ejection time can also be determined for the right ventricle (RVET) which can form a quotient with PEP for demonstrating heart insufficiency.

Figure 19:
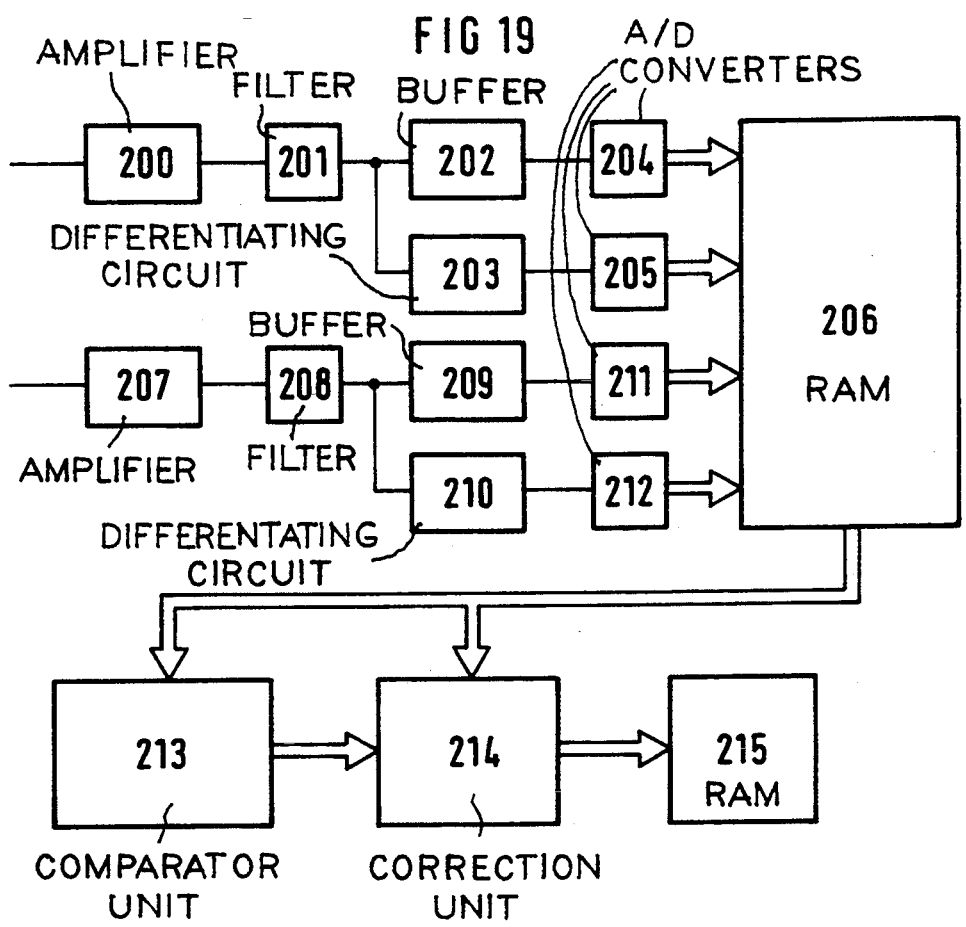
FIG. 19 shows a block diagram of a seventh embodiment of the device, used as a noise filter.

A noise filter, described in FIG. 19 and based on the pacemaker in FIG. 17, can also be devised with, e.g., the ECG signal as an input signal to a first amplifier 200, the amplified signal being filtered in a first filter 201 and then being fed to a first buffer 202 and to a first differentiating circuit 203. The buffered signal and the differentiated signal are respectively digitized in a first A/D converter 204 and a second A/D converter 205 whose outputs are then sent to a RAM 206. The pressure signal is simultaneously used as an input signal for a second amplifier 207, passes a second filter 208 and is then sent to a second buffer 209 and a second deriving circuit 210. The output of those components are respectively supplied to a third A/D converter 211 and a fourth A/D converter 212, whose outputs are also fed to the RAM 206. All four related values are then sent to a comparator unit 213 in which they are compared to previously stored sequences. Since the two input signals have different origins, one electrical and one mechanical heart variable, they are affected by different kinds of noise. When the signals are subjected to parallel comparison in this way, noise can be identified when one signal is affected but not the other. Different noises can be separated and sent to a correction unit 214 to which the related values are also sent from the RAM 206 for correction. Corrected values are sent to a second RAM 215 for subsequent analysis, e.g., in one of the above-described ways.

Figure 20:
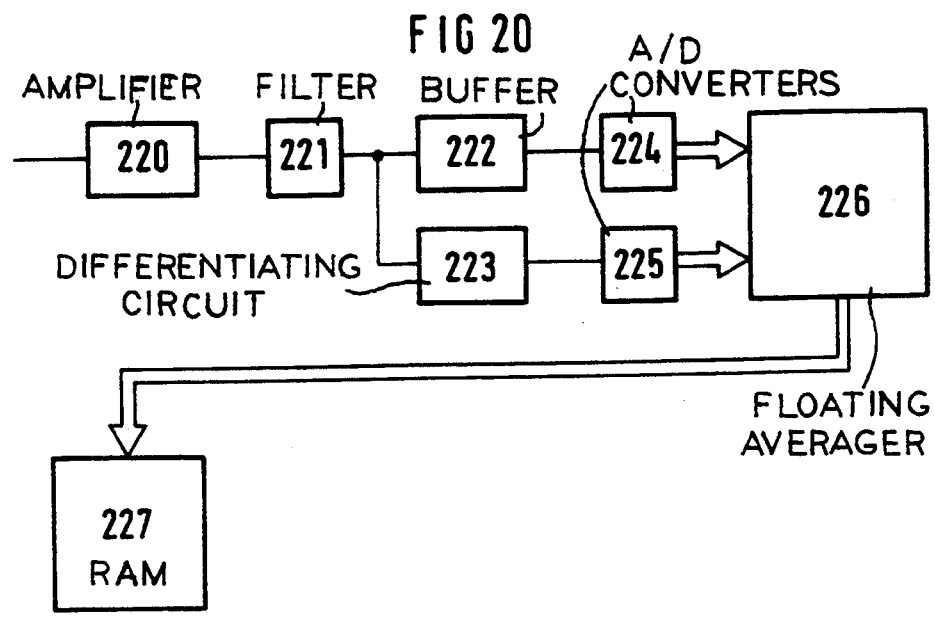
FIG. 20 shows a block diagram of an eighth embodiment of the device, used as a noise filter.

Another kind of filter which can be obtained in accordance with the present invention is shown in FIG. 20. As before, the input signal is fed to an amplifier 220 and a filter 221 before being transferred to a buffer 222 and to a differentiating unit 223. The signals are digitized in a first A/D converter 224 and a second A/D converter 225 respectively before being fed to a floating averager 226 which over a given period of time calculates the average value for the curve formed by the two signals. The average values are then sent to a sequential RAM 227 for additional signal conditioning. This filtration can also be performed on two separately received measurement signals.

Figure 21:
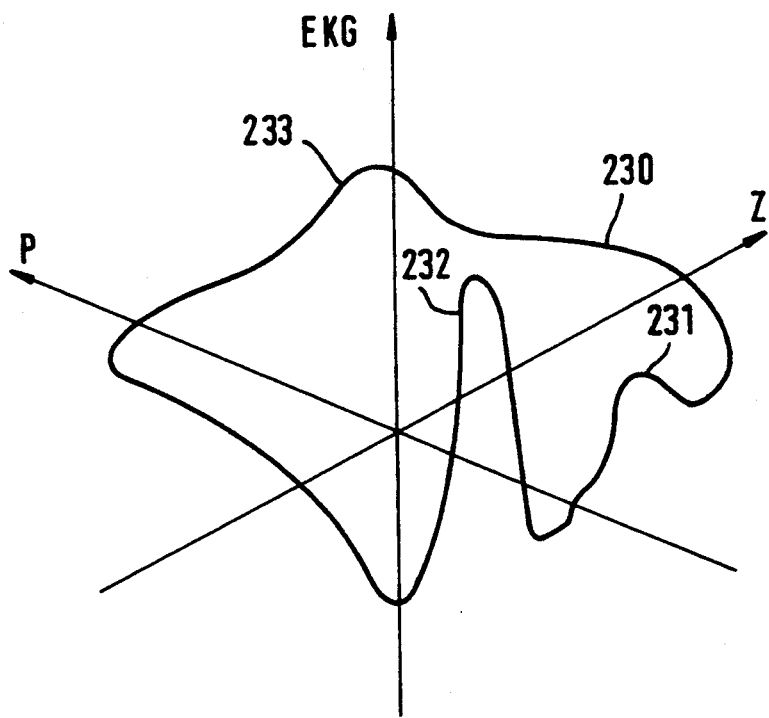
FIG. 21 illustrates in the form of a coordinate system diagram the function of a ninth embodiment of the device.

FIG. 21 shows a three-dimensional coordinate system with an impedance axis Z, a pressure axis P and an ECG axis ECG. The signals can be supplied by e.g., the pacemaker 170 in FIG. 17. The impedance-pressure-ECG curve 230 obtained can then be analyzed to control a pacemaker or in the diagnosis of heart diseases or other anomalies in the heart. Certain characteristic parts of the impedance-pressure-ECG signal are easy to recognize, such as the P wave 231, the QRS complex 232 and the T wave 233. In principle, the impedance-pressure curve 195 in FIG. 18 corresponds to a projection of the impedance-pressure-ECG curve 230 in the impedance-pressure plane Z-P, and any reduction in this curve along the pressure axis indicates that the heart in question is no longer pumping any blood, even if the ECG signal may itself be virtually unchanged. Different areas (or volumes) can be entered into this coordinate system Z-P-ECG. The analysis can then be performed so that the areas traversed by the curve and the sequence in which the areas are traversed are recorded and compared to previously recorded sequences.

FIG. 22 shows another version of the manner by which the invention creates an opportunity for effective analysis of signals originating in the heart. A pacemaker 240 is connected to a heart 241, as previously described, with a tip electrode 242 and a ring electrode 243 connected, via a first electrode conductor 244 and a second electrode conductor 245, to a pulse generator 246. A detector 247 is connected in parallel across the pulse generator 246. A pressure sensor 248 is also placed in the ventricle of the heart 241 and transfers 30 signals, via a first signal conductor 249, to a pressure detector 250. An acoustic sensor 251 senses heart sounds, e.g., valve noise, and transfers signals corresponding to the heart sounds to an acoustic detector 253 via a signal conductor 252. The measurement signals picked up by the detectors 247, 250 and 253 are transferred to a signal analysis unit 254 for analysis. The signal analysis unit 254 communicates with a control unit 255 which, in turn, controls the pulse generator 246 and the detectors 247, 250 and 253.

Via a telemetry unit 256, as previously described, a physician can exchange information with the pacemaker via a programming unit 257.

In this instance, the recorded heart sounds are used as sub-conditions for the signal analysis to which impedance and pressure signals are subjected. In, e.g., area analysis of the signal, one condition could be that the impedance-pressure curve should be in a particular area at the second heart sound for function to be regarded as normal. Heart sounds can also be used to start or stop timings.

In the above embodiments, the analysis of heart function with ECG, impedance, pressure and heart sounds has been described in conjunction with an ECG apparatus and different kinds of implantable pacemakers. Combining the described embodiments in different ways and even using other heart signals, such as blood flow and heart wall movements, is naturally fully possible. The invention can further be implemented in other devices such as cardioverters, defibrillators and implantable heart detectors.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for analyzing the function of a heart comprising:
    measurement means for measuring a heart variable and for generating a measurement signal related to said heart variable;
    parameter signal generator means for generating a parameter signal related to a heart variable, said parameter signal and said measurement signal having related values; and
    evaluation means for identifying and analyzing said related values of said measurement signal and said parameter signal and for generating an analysis result indicative of the functioning of said heart by plotting said measurement signal against said parameter signal to obtain a curve having a morphology and a chronological course, and means for analyzing said morphology and chronological course of said curve.

2. An apparatus as claimed in claim 1 wherein said means for generating a parameter signal comprises means for differentiating said measurement signal to obtain a differentiated signal serving as said parameter signal.

3. An apparatus as claimed in claim 1 wherein said means for generating a parameter signal comprises measurement means for measuring a further heart variable and for generating a further measurement signal related to said further heart variable, said further measurement signal serving as said parameter signal.

4. An apparatus as claimed in claim 1 further comprising further measurement means for measuring a further heart variable and for generating a further measurement signal relative to said further heart variable, said measurement signal, said further measurement signal and said parameter signal having related values, and wherein said evaluation means comprises means for identifying and analyzing said related values of said measurement signal, said further measurement signal and said parameter signal and for generating an analysis result indicative of the functioning of said heart.

5. An apparatus as claimed in claim 1 further comprising:
    comparator means for continuously comparing said related values for detecting drift of said related values; and
    compensation means, supplied with an output from said comparator means, for compensating current related values for any drift identified by said comparator means.

6. An apparatus as claimed in claim 1 further comprising:
    means for storing at least one set of said related values respectively associated with a previously obtained measurement signal and a previously obtained parameter signal;
    means for respectively comparing said stored related values to current related values respectively associated with a current measurement signal and a current parameter signal for identifying noise in said current related values if a noise change is present in one of said current related values without an equivalent change being present in the other of said current related values; and
    means for compensating a current related value in which noise is identified for the noise identified therein.

7. An apparatus as claimed in claim 1 wherein said evaluation unit comprises:
    means for plotting said measurement signal against said parameter signal to obtain a curve exhibiting an arc length; and
    means for measuring said arc length, said arc length serving as said analysis result indicative of the functioning of said heart.

8. An apparatus as claimed in claim 7 wherein said means for plotting comprises means for plotting said measurement signal against said parameter signal over one cardiac cycle of said heart.

9. An apparatus as claimed in claim 1 wherein said measurement means comprises means for measuring impedance in said heart and for generating an impedance signal serving as said measurement signal.

10. An apparatus as claimed in claim 9 wherein said parameter signal generator means comprises means for differentiating said impedance signal to obtain a differentiated impedance signal, said differentiated impedance signal serving as said parameter signal.

11. An apparatus as claimed in claim 1 wherein said evaluation means comprises means for plotting said measurement signal against said parameter signal to obtain a curve, and area calculator means for calculating an area, substantially enclosed by said curve, the calculation of said area serving as said analysis result indicative of the functioning of said heart.

12. An apparatus as claimed in claim 11 wherein said area calculator means comprises means for calculating an area substantially enclosed by said curve for each cardiac cycle.

13. An apparatus as claimed in claim 1 wherein said evaluation unit comprises means for plotting said measurement signal against said parameter signal to obtain a curve, and distance calculator means for calculating a distance between selected points on said curve, said distance serving as said analysis result indicative of the functioning of said heart.

14. An apparatus as claimed in claim 13 wherein said distance calculator means comprises means for calculating a distance between selected maximum and minimum points on said curve.

15. An apparatus as claimed in claim 1 wherein said evaluation means comprises means for plotting said measurement signal against said parameter signal to obtain a curve, memory means for storing said curve for each cardiac cycle of said heart, and comparator means for comparing said curve to obtain a comparison result, said comparison result serving as said analysis result indicative of the functioning of said heart.

16. An apparatus as claimed in claim 15 wherein said predetermined curve is a curve obtained by said means for plotting said measurement signal against said parameter signal, for a previous cardiac cycle.

17. An apparatus as claimed in claim 15 further comprising means for supplying a programmed curve to said comparator for use as said predetermined curve.

18. An apparatus as claimed in claim 1 wherein said evaluation means comprises memory means for storing the course of said related values over a selected period of time, and comparator means for comparing said stored course of related values with at least one predetermined course to obtain a comparison result, said comparison result serving as said analysis result indicative of the functioning of said heart.

19. An apparatus as claimed in claim 18 wherein said evaluation means further comprises memory means for storing a course of said related values over an earlier selected period of time for use as said predetermined course.

20. An apparatus as claimed in claim 18 further comprising means for supplying a programmed course of related values to said comparator means for use as said predetermined course.

21. An apparatus as claimed in claim 1 wherein said evaluation means comprises memory means for storing a course in a coordinate system of said related values over a selected period of time, and means for identifying a sequence in which said stored course traverses a selected number of areas in said coordinate system, and comparator means for comparing said sequence with a predetermined sequence to obtain a comparison result, said comparison result serving as said analysis result indicative of the functioning of said heart.

22. An apparatus as claimed in claim 21 wherein said evaluation means further comprises memory means for storing a sequence obtained over an earlier selected period of time for use as said predetermined sequence.

23. An apparatus as claimed in claim 21 further comprising means for supplying a programmed sequence to said comparator means for use as said predetermined sequence.

24. An apparatus for analyzing the function of a heart comprising:
  measurement means for measuring a heart variable and for generating a measurement signal related to said heart variable;
  parameter signal generator means for generating a parameter signal related to a heart variable, said parameter signal and said measurement signal having related values;
  evaluation means for identifying and analyzing said related values of said measurement signal and said parameter signal and for generating an analysis result indicative of the functioning of said heart; and
  averaging means for continuously calculating an average of at least one of said related values over a predetermined period of time.

25. An apparatus as claimed in claim 24 wherein said evaluation means comprises means for plotting said measurement signal against said parameter signal to obtain a curve having a morphology, and means for analyzing said morphology of said curve.

26. An apparatus as claimed in claim 24 wherein said evaluation means comprises means for plotting said measurement signal against said parameter signal to obtain a curve having a chronological course, and means for analyzing said chronological course of said curve.

27. An apparatus as claimed in claim 24 wherein said evaluation means comprises means for plotting said measurement signal against said parameter signal to obtain a curve having a morphology and a chronological course, and means for analyzing said morphology and chronological course of said curve.

28. An apparatus for analyzing the function of a heart comprising:
  measurement means for measuring impedance in a heart for generating an impedance signal;
  parameter signal means for generating a parameter signal by differentiating said impedance signal;
  means for plotting said impedance signal against said parameter signal to obtain a curve;
  arc length calculator means for calculating an arc length of said curve for each cardiac cycle of said heart;
  a plurality of comparators to which the calculated arc length is supplied, each comparator comparing the calculated arc length to a respectively different predetermined arc length and each comparator generating an output signal if the calculated arc length exceeds the respective predetermined arc length; and
  computer means for determining whether said heart is hemodynamically stable based on the outputs of said comparators.

* * * * *